United States Patent
Kato

(10) Patent No.: US 9,480,509 B2
(45) Date of Patent: Nov. 1, 2016

(54) OSTEOSYNTHESIS APPARATUS FOR PROXIMAL FEMUR FRACTURE AND MASTER SCREW-TYPE SCREW APPARATUS FOR OSTEOSYNTHESIS APPARATUS FOR PROXIMAL FEMUR FRACTURE

(71) Applicant: FOUR STUDIES LTD., Ageo-shi, Saitama (JP)

(72) Inventor: Shigetoshi Kato, Ageo (JP)

(73) Assignee: FOUR STUDIES LTD., Ageo-Shi (JP)

( * ) Notice: Subject to any disclaimer, the term of this patent is extended or adjusted under 35 U.S.C. 154(b) by 0 days.

(21) Appl. No.: 14/894,597

(22) PCT Filed: Jul. 25, 2014

(86) PCT No.: PCT/JP2014/069665
§ 371 (c)(1),
(2) Date: Nov. 30, 2015

(87) PCT Pub. No.: WO2015/068434
PCT Pub. Date: May 14, 2015

(65) Prior Publication Data
US 2016/0128743 A1    May 12, 2016

(30) Foreign Application Priority Data

Nov. 7, 2013    (JP) .................................. 2013-243312
Mar. 17, 2014   (JP) .................................. 2014-077331

(51) Int. Cl.
*A61B 17/74*    (2006.01)
*A61B 17/17*    (2006.01)

(52) U.S. Cl.
CPC .......... *A61B 17/744* (2013.01); *A61B 17/1721* (2013.01); *A61B 17/74* (2013.01)

(58) Field of Classification Search
CPC .......................................... A61B 17/74–17/748
USPC ....................................................... 606/62–68
See application file for complete search history.

(56) References Cited

U.S. PATENT DOCUMENTS

2002/0156473 A1* 10/2002 Bramlet ............... A61B 17/744
                                                                    606/62
2009/0275994 A1  11/2009 Phan et al.
(Continued)

FOREIGN PATENT DOCUMENTS

JP    2001-286480 A    10/2001
JP    2002-505906 A    2/2002
(Continued)

OTHER PUBLICATIONS

ISA/JP Authorized Officer, Tomoya Sato, International Search Report issued on Nov. 18, 2014 in International Application No. PCT/JP2014/069665, total 6 pages with translation.
(Continued)

*Primary Examiner* — Nicholas Plionis
(74) *Attorney, Agent, or Firm* — Masuvalley & Partners

(57) ABSTRACT

Embodiments of the present invention provide an osteosynthesis apparatus for proximal femur fractures. The osteosynthesis apparatus for proximal femur fractures has a structure in which a lag screw set and a nail are assembled via screwing process. The lag screw is assembled with a key ring and a fastening nut in advance. When inserting this lag screw set into a bone, grip bars are inserted radially at a predetermined angle and direction, resulting in a strong bone holding power. Further, in a final step, a strong fixed coupling is achieved by forcibly screwing and engaging the lag screw and the fastening nut by an interference of the threads of the lag screw and the fastening nut. Thus, the osteosynthesis apparatus for proximal femur fractures has a strong bone holding power and is stable without loosening.

7 Claims, 23 Drawing Sheets

(56) References Cited

U.S. PATENT DOCUMENTS

2009/0326534 A1    12/2009    Yamazaki et al.
2012/0191092 A1    7/2012    Buettler et al.
2013/0041414 A1    2/2013    Epperly et al.

FOREIGN PATENT DOCUMENTS

| | | |
|---|---|---|
| JP | 2003-284730 A | 10/2003 |
| JP | 2005-509453 A | 4/2005 |
| JP | 2007-090094 A | 4/2007 |
| JP | 2007-236568 A | 9/2007 |
| JP | 2011-115408 A | 6/2011 |
| JP | 2013-063268 A | 4/2013 |
| WO | 99/45858 A1 | 9/1999 |
| WO | 02/085219 A2 | 10/2002 |
| WO | 2004/039270 A1 | 5/2004 |
| WO | 2012/099944 A1 | 7/2012 |

OTHER PUBLICATIONS

EPO, Extended European Search Report issued on Apr. 28, 2016 in the EP Patent Application No. 14860728.6 (corresponding to PCT/JP2014/069665), total 6 pages.

\* cited by examiner

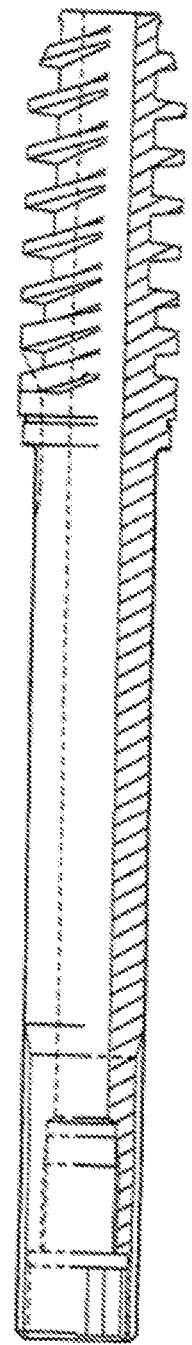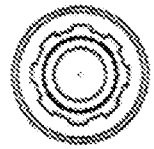
FIG. 25

OSTEOSYNTHESIS APPARATUS FOR PROXIMAL FEMUR FRACTURE AND MASTER SCREW-TYPE SCREW APPARATUS FOR OSTEOSYNTHESIS APPARATUS FOR PROXIMAL FEMUR FRACTURE

This application is the U.S. National Phase of and claims priority to International Patent Application No. PCT/JP2014/069665, International Filing Date Jul. 25, 2014, entitled Osteosynthesis Device For Proximal Femur Fracture And Master Screw Type Screw Device For Osteosynthesis Device For Proximal Femur Fracture, which claims benefit of Japanese Patent Application No. 2013-243312 filed Nov. 7, 2013 and Japanese Patent Application No. 2014-077331 filed Mar. 17, 2014, which are hereby expressly incorporated by reference in their entirety for all purposes.

TECHNICAL FIELD

This invention relates to a structure of a lag screw set for implant mainly used in osteosynthesis operation of proximal femur fracture and a fixation mechanism of a nail and a lag screw. Also, this invention relates to a driving apparatus attached to a guide apparatus body (frame) for an osteosynthesis apparatus for proximal femur fracture, and particularly relates to a driving apparatus for an osteosynthesis apparatus used in osteosynthesis operation for proximal femur fracture, the driving apparatus having a structure capable of screwing a lag screw via a master screw.

BACKGROUND OF THE DISCLOSURE

An intramedullary fixation method for operation on proximal femur fracture is conventionally known, wherein the method uses a nail inserted into a femur diaphysis from a bone head in a vertical downward direction and a lag screw obliquely inserted into a through hole located at an upper side of the nail.

Also, a fixing structure for fixing a nail and a lag screw by utilizing a pressing force generated by screwing a stopper screw, which is a lag screw having a bite-in thread at a front end portion thereof, is conventionally known. In this fixing structure described in Japanese Patent Application No.: JP 2007-236568 A (hereinafter Patent Document 1), a method for fastening a screw and a method for preventing rotation of a screw, which utilize a conventional art in a normal way, are used.

Meanwhile, the above-described intramedullary fixation method directly rotates a lag screw via a guide apparatus for bone surgery to advance the lag screw according to a lead of the lag screw toward a bone head suffering fracture and perform threading, and then holds the lag screw. It is sometimes difficult, however, to create a thread by threading due to a density of a cancellous bone.

Such guide apparatus for bone surgery that executes threading by directly rotating a lag screw is commonly known as a target device. The target apparatus includes an arc-shaped guide apparatus body (frame) coupled to a base portion of a nail by screwing and a guide sleeve fixedly connected to the frame, and the frame includes a connecting portion at which the frame is connected to the base portion of the nail and a guide portion extending substantially in parallel with the nail so as to create a predetermined constant gap between the connecting portion and the guide portion. The guide sleeve is fixedly connected to the guide portion of the frame and is held via the frame in a position confronting a transversal hole provided on the nail, so that various tools and bone surgery equipment such as a bone connection tool are inserted into and guided through the guide sleeve. As an example of this kind of guide apparatus, Japanese Patent Application No.: JP 2011-115408 A (hereinafter Patent Document 2) discloses a guide apparatus for attaching an osteosynthesis device, the apparatus includes a nail introduced into a marrow of a femur and a lag screw inserted into a bone head part of the femur so as to intersect with the nail.

The above-described fixing structure, however, has a problem in that fastening achieved by the structure could become loosened and is thus unstable, because the structure substantially utilizes only a pressing force from an end portion of the lag screw. Another problem is that a bone holding power merely achieved by a holding power of a screw is not sufficient for fixing a bone suffering severe osteoporosis.

SUMMARY OF THE INVENTION

An object of the present invention, which has been achieved in consideration of the above-described circumstances, is to enable swift and highly stable insertion of a lag screw into a cancellous bone and assembly of the lag screw to a nail by easily screwing a lag screw set. The lag screw set may include the lag screw, a key ring, and a fastening nut anteriorly in an axial direction while the lag screw set is guided by a key groove with respect to the nail. Further object of the present invention is to achieve a strong bone holding power, anti-rotation of the lag screw due to a forced fixing to the fastening nut, and a mechanism for retaining the lag screw set by radially inserting grip bars into the cancellous bone in an outer circumferential direction of the lag screw at the same time.

Also, the above-described conventional guide apparatus for bone surgery has problems, such as: creating a thread by means of threading is sometimes difficult due to a density of a bone interior portion; a front end portion of the lag screw having a thread is not stably maintained in a bone head part, or the lag screw cannot be pulled off when such need arises once the lag screw is fixed by threading; and inserting various surgical tools into the guide apparatus in an alternating manner is cumbersome and hinders surgery.

In order to address these problems, a second aspect of the present invention provides a screw apparatus for osteosynthesis apparatus for proximal femur fracture that is capable of executing threading regardless of a bone density of a bone head part, reliably holding a lag screw in a set position in a marrow, pulling out the lag screw as needed, and enabling easy, swift, and precise insertion and extraction of surgical tools.

<First Invention: Osteosynthesis Apparatus for Proximal Femur Fracture>

An assembly structure of a nail and a lag screw according to the embodiments of the present invention is configured as follows: First, a front end outer circumferential portion of a fastening nut is fixedly engaged with a fixing groove at a rear inner circumferential portion of a key ring so that the fastening nut and the key ring are rotatable with respect to each other. Then, a rear end of a lag screw, into which a guide ring for grip bars is press-fitted and caulked in advance, is slidingly fitted into an inner circumferential hole of a set of the key ring and the fastening nut. This is performed from forward in an axial direction and is stopped at a position where the rear end of the lag screw is in contact with a female thread of the fastening nut. Next, a male thread at a rear portion of the lag screw is engaged with the female thread of the fastening nut up to a predetermined point to create a lag screw set in which the lag screw, the key ring, and the fastening nut are integrally combined. The lag screw set is then inserted into the nail along a key groove of the nail so that the lag screw set and the nail are engaged with key.

A turning tool is inserted into a driving hole, such as a spline, at the rear end portion of the lag screw and is rotated to advance the lag screw set to a predetermined position. The turning tool is then inserted into a driving hole, such as a female spline, at a rear portion of the fastening nut and is rotated. In response to the rotation, the key ring advances, and front end portions of the grip bars come into contact with axially aligned grooves formed in the rear of a thread end portion of a single to triple thread of the lag screw in accordance with a predetermined angle of groove bottom portions of the grooves and then expand in an outer circumferential direction. When the fastening nut is further rotated, the front end portions of the grip bars sequentially come into contact with a side surface of the single to triple thread in a spiral manner such that the grip bars are inserted while maintaining predetermined open angles. Both side surfaces of a groove provided on a cylindrical projection of the lag screw and side surface root portions of each of the grip bars of the key ring fit and mesh with each other.

The lag screw set is then fixed by forcibly rotating the fastening nut so that a trailing end portion of the female thread of the fastening nut and a trailing end portion of a male thread of the lag screw constituting an interference are forcibly fixed by screwing. Accordingly, this assembly structure is unique in that the structure is configured by combining the nail and the lag screw set integrally including the lag screw, the key ring, and the fastening nut. The osteosynthesis apparatus for proximal femur fracture having the above-described configuration consists of a small number of components, is simple, and enables the lag screw included in the lag screw set to be easily screwed while being guided by the nail with the key in a short period of time with relatively light force by inserting a normal turning tool into a driving spline or the like of the lag screw and rotating the turning tool.

By finally fixing the lag screw with the turning tool and rotating the fastening nut with a turning tool for the fastening nut, a part of the female thread of the fastening nut is forcibly meshed and fixed with a part of the male thread of the lag screw constituting the interference. Therefore, the rotational fixing of the lag screw set does not loosen, and thus the lag screw is stably locked in a rotating direction and maintains a high stability in a resting state that does not loosen permanently. Also, because a projection provided at a rear end portion of the fastening nut prevents the lag screw from moving and then coming out of the nail in a forward direction, the lag screw set and the nail ensure high safety and long-term stability.

<Second Invention: Master Screw-Type Screw Apparatus>

A screw apparatus according to the second embodiment of the present invention includes a frame according to a conventional art. In addition, instead of directly rotating and advancing a lag screw for threading by the lag screw, the screw apparatus includes, on the basis of a master screw mechanism, a hollow boss portion fixed to an operation-side end portion of the frame and having a master screw female thread formed at an inner circumferential portion thereof. A master screw driving knob having a master screw male thread capable of meshing with the master screw female thread is then rotated while the master screw male thread and the master screw female thread are meshed with each other. This enables the lag screw set coupled to the master screw driving knob with spline or the like to be guided and advanced according to the same lead as the master screw male thread. Thus, precise screwing can be performed with light operating force.

In this embodiment, the screw apparatus for a lag screw is operated by the following steps: First, as a preliminary step, a frame 11 of a conventional art is fixed to a nail 16 with a coupling bolt 18 by using a conventional method in a predetermined direction. Next, a stationary receiving boss 12 in which a master screw female thread has a large size so as not to interfere with other tools is fixed to an operation-side end portion of the frame 11 by screwing or the like. A master screw driving knob 3 having a master screw male thread coupled to a lag screw set 17 with spline or the like is then meshed with the master screw female thread of the stationary receiving boss 12, and the lag screw set 17 is screwed into a predetermined position to complete a screwing operation. Finally, the coupling bolt 18 is loosened and removed in a conventional way and the frame 11 is detached from the nail 16.

As described above, the assembly structure of the nail and the lag screw according to the embodiments of the present invention is advantageous in that the nail and the lag screw set can be easily and highly stably assembled to each other in a short period of time along an axial direction only so as not to loosen permanently. The assembly structure also includes a mechanism for retaining the lag screw. Thus, it is possible to stably fix a proximal portion of a femur suffering a fracture without using expert skill.

Also, a master screw female thread is formed in the stationary receiving boss 12 at the operation-side end portion opposing a nail-side end portion of the arc-shaped frame 11, and a master screw driving knob 13 having a master screw male thread capable of meshing with the master screw female thread is manually rotated while the lag screw set 17 having a drill cutter at a front end thereof is coupled to the master screw driving knob 13 with spline or the like. This enables to advance the lag screw set 17 according to the same lead as the master screw male thread and to execute tapping accurately. At the same time, the tapping can be executed directly and reliably without creating a prepared hole for the thread of the lag screw in a cancellous bone of a bone head part.

BRIEF DESCRIPTION OF DRAWINGS

The present disclosure is described in conjunction with the appended figures:

FIG. 25 is a general view of an embodiment of a lag screw set in accordance with a second aspect of the present invention.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

First Invention

Osteosynthesis Apparatus for Proximal Femur Fracture

Figure 1:
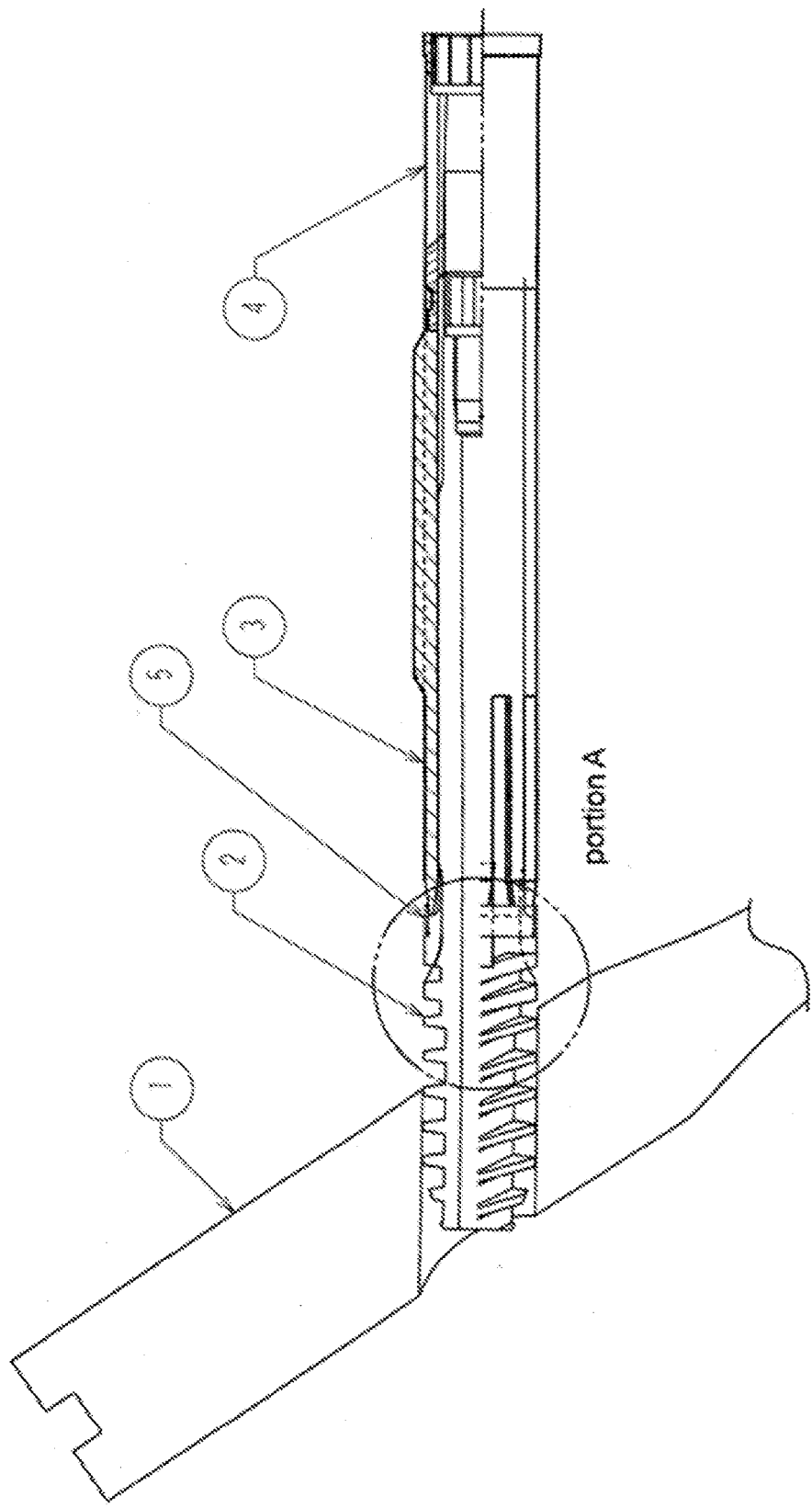
FIG. 1 is a general cross-sectional view illustrating an embodiment of a "state of insertion" of a lag screw set into a nail.
Figure 2:
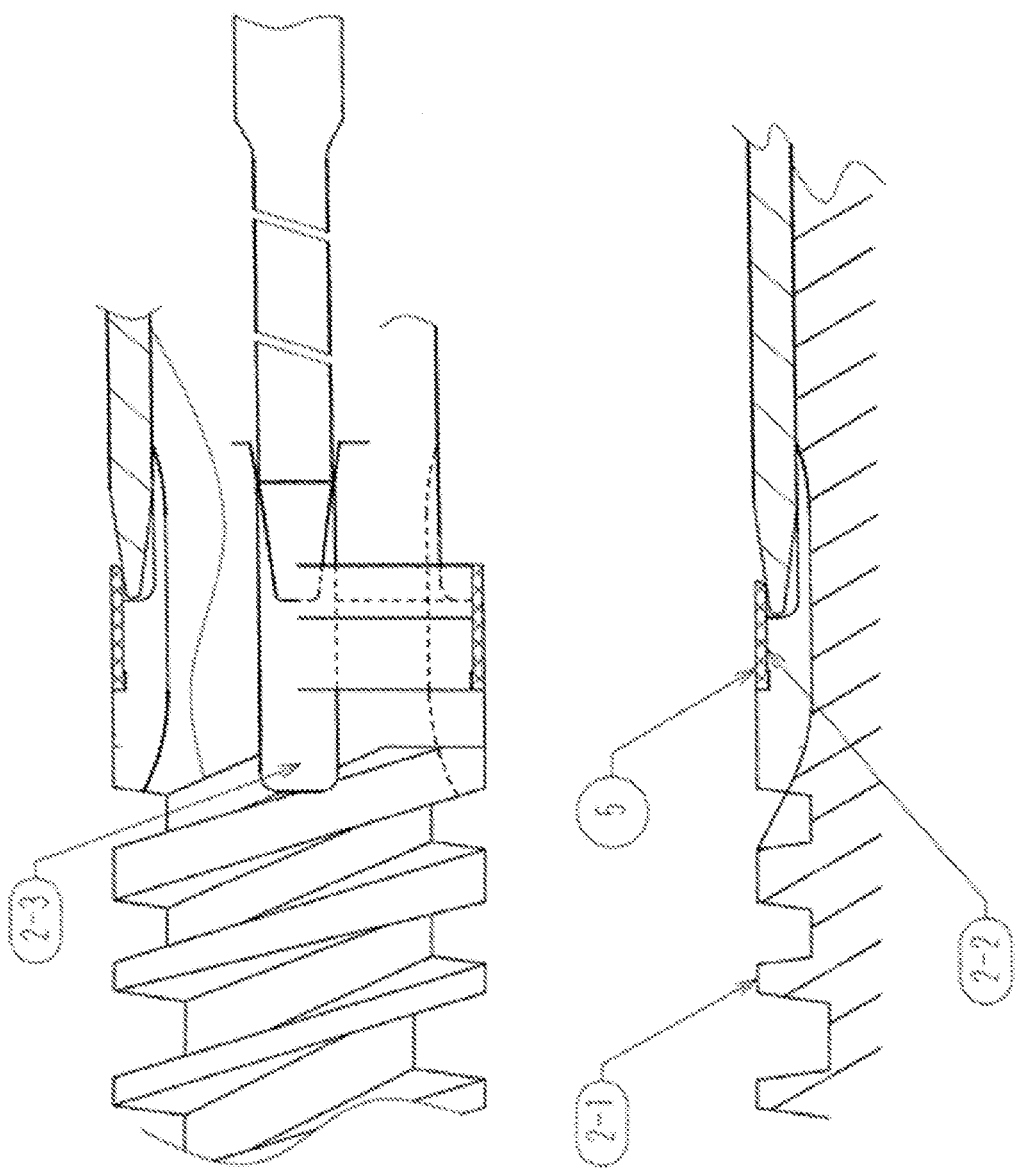
FIG. 2 is an enlarged detailed view of portion A in FIG. 1, illustrating a grip bar guide groove of a lag screw and a grip bar that is not yet open.
Figure 3:
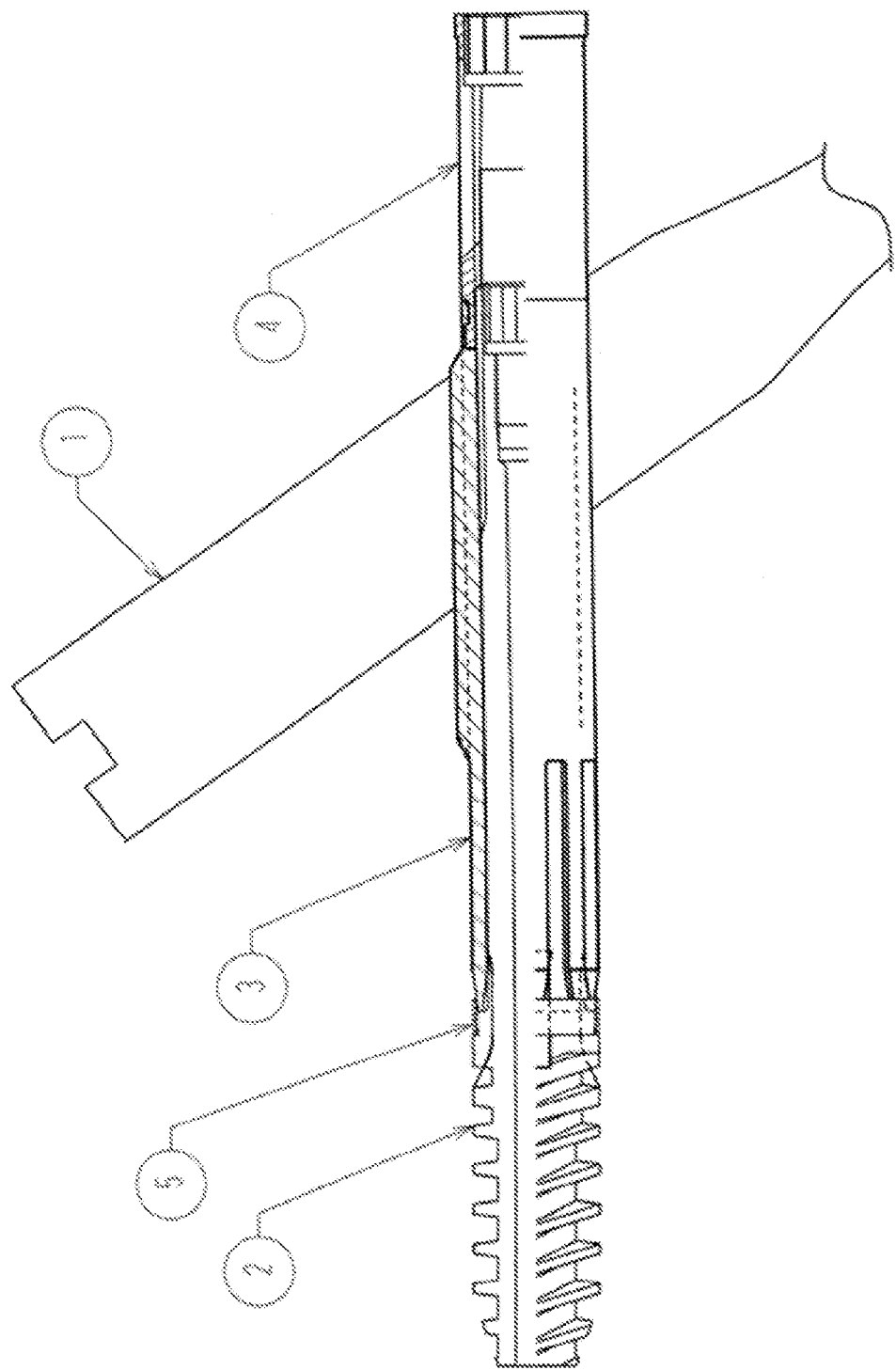
FIG. 3 is a diagram of an embodiment illustrating a state in which the lag screw set is screwed into a predetermined position.
Figure 4:
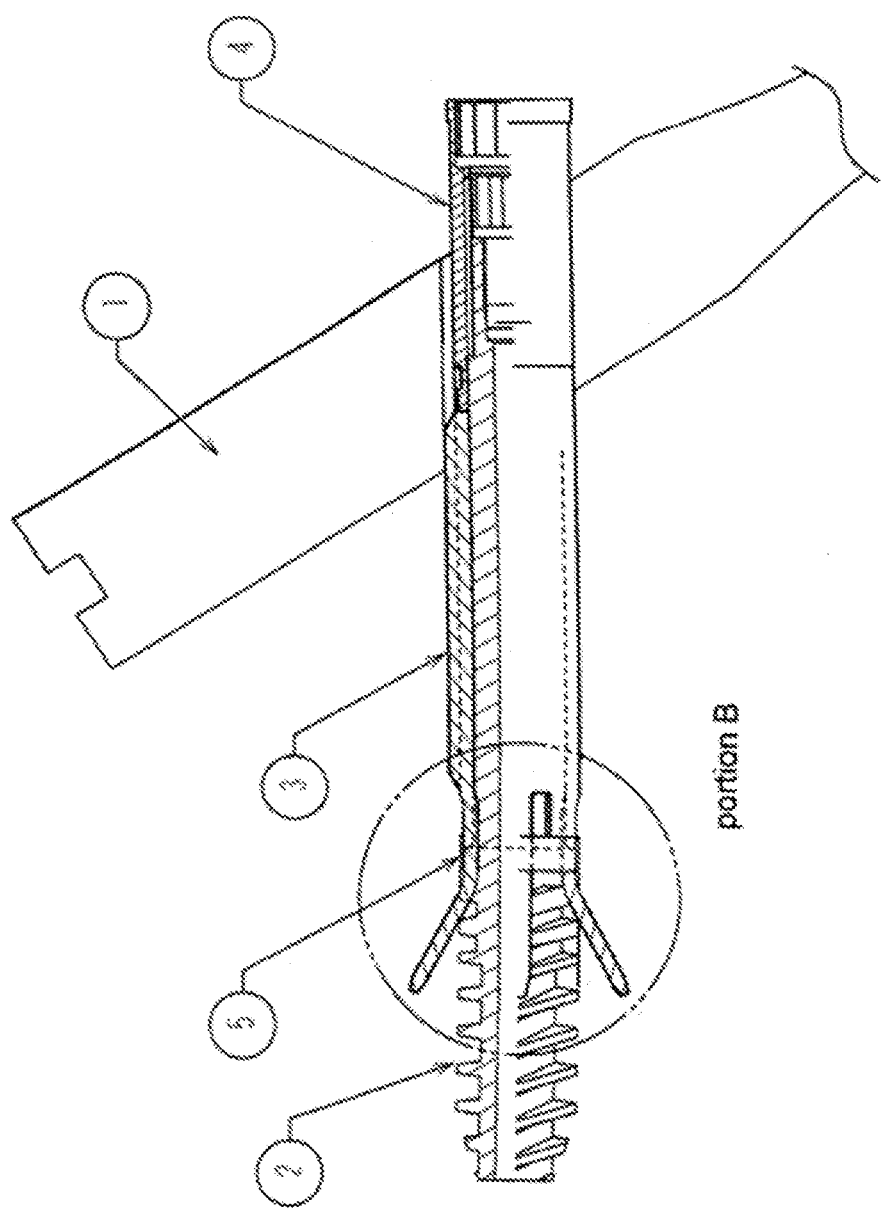
FIG. 4 is a diagram of an embodiment illustrating a final state in which grip bars are open at a lock advance end of the lag screw.
Figure 5:
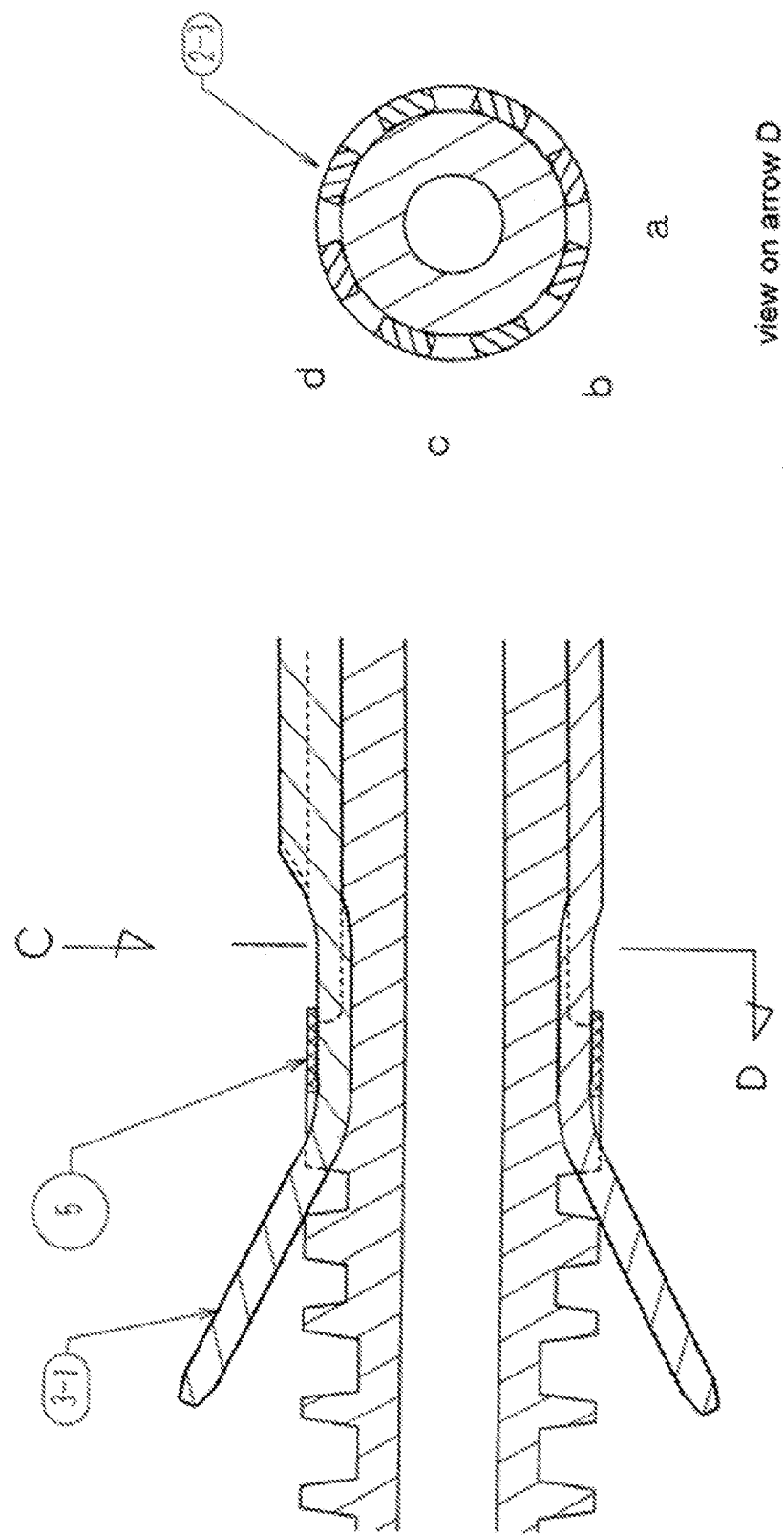
FIG. 5 is an enlarged detailed view 1 of portion B in FIG. 4, illustrating grip bar guide grooves of the lag screw and the grip bars in a final open state.
Figure 6:
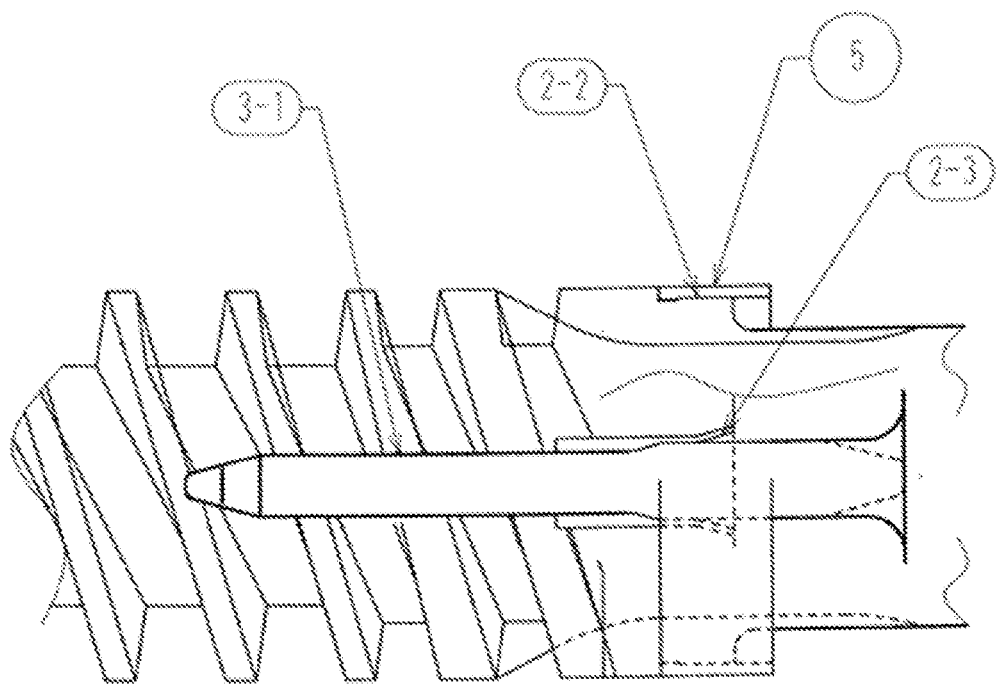
FIG. 6 is a view taken along arrow C of FIG. 5, illustrating a state where the grip bar is engaged with the grip bar guide groove.
Figure 7:
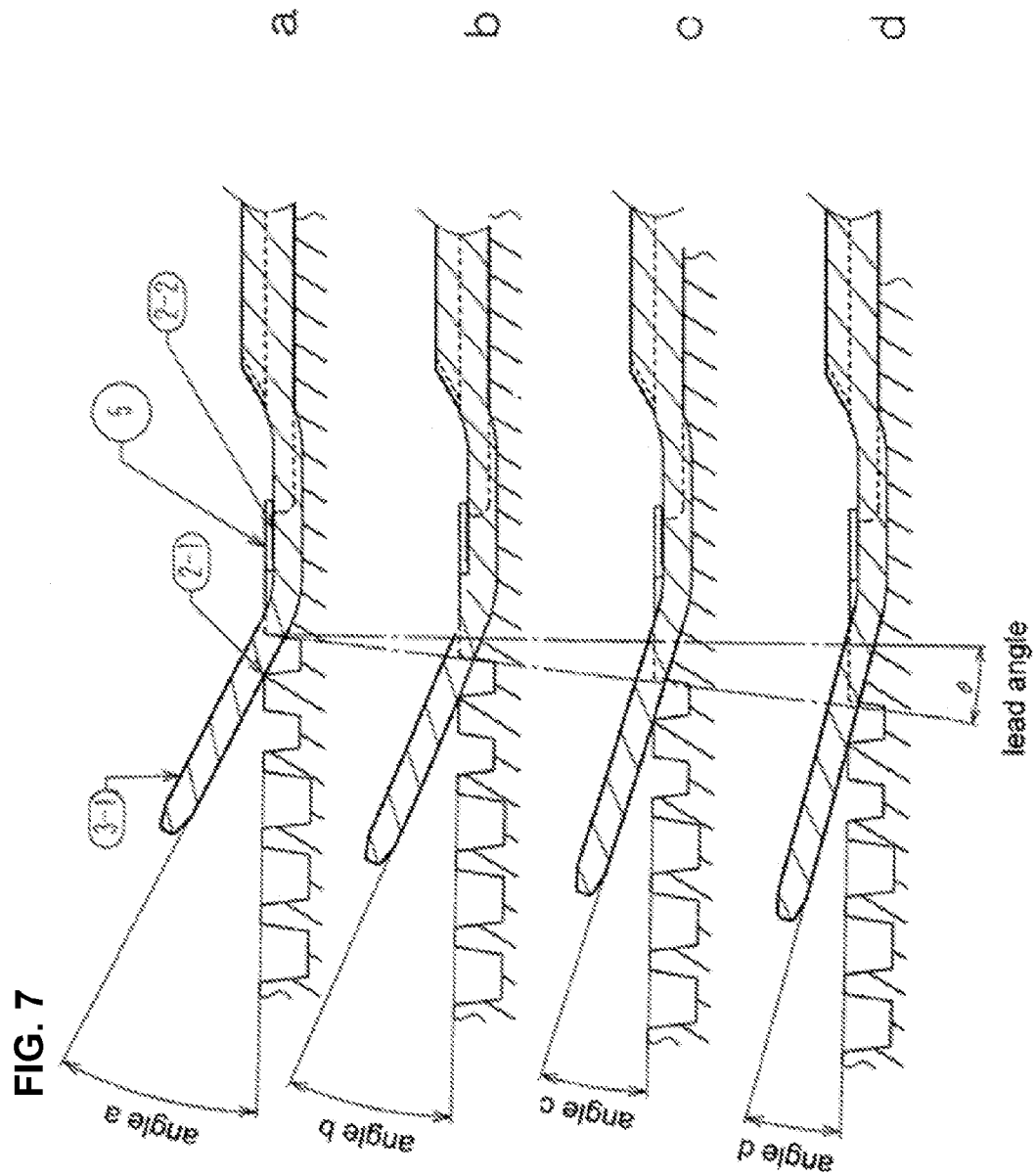
FIG. 7 is an enlarged detailed view 2 of portion B in FIG. 4, illustrating cross sections of grip bar guide grooves a, b, c, and d of the lag screw.
Figure 8:
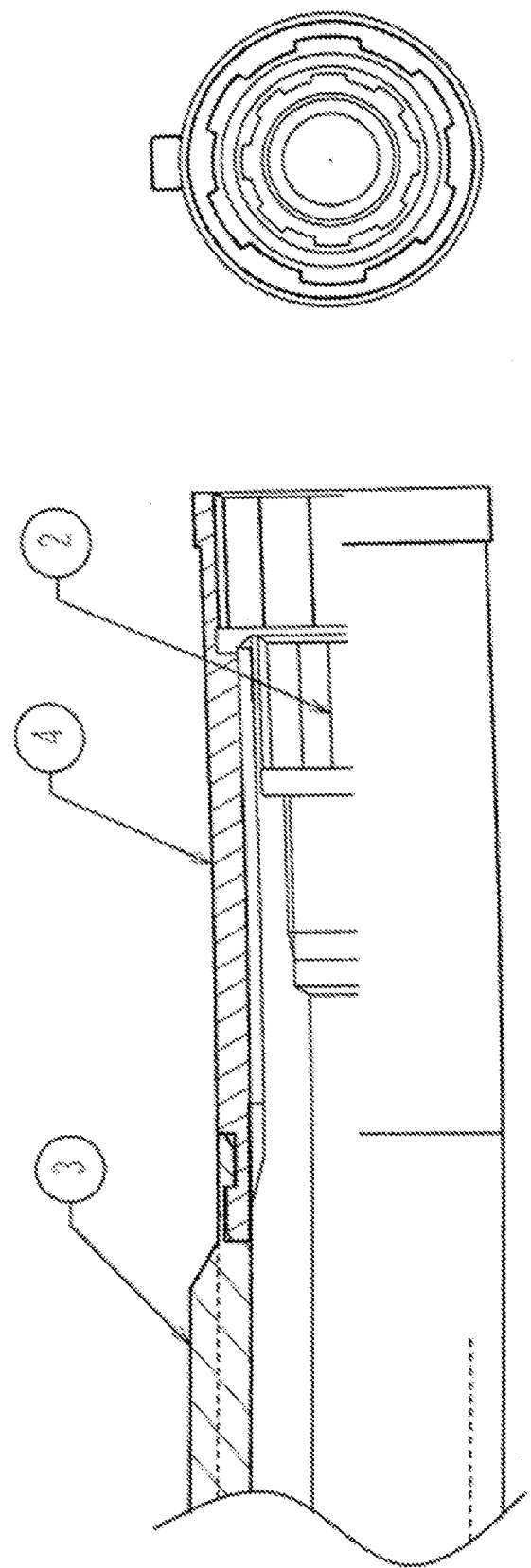
FIG. 8 is a cross-sectional view illustrating coupling between the lag screw, a key ring, and a fastening nut according to the first embodiment of the present invention.
Figure 9:
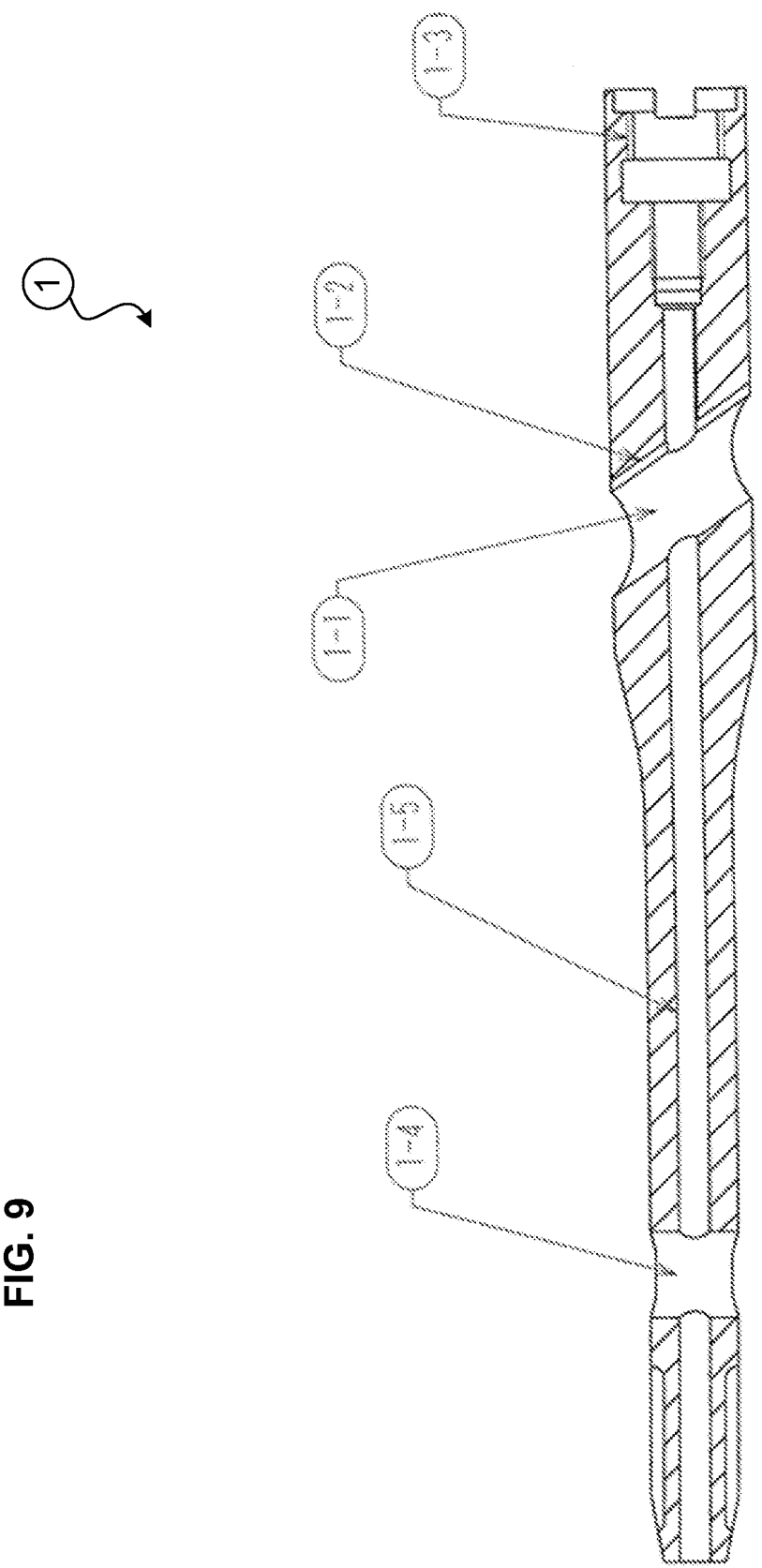
FIG. 9 is a cross-sectional view of a nail of known art used in the one embodiment of the first invention.
Figure 10:
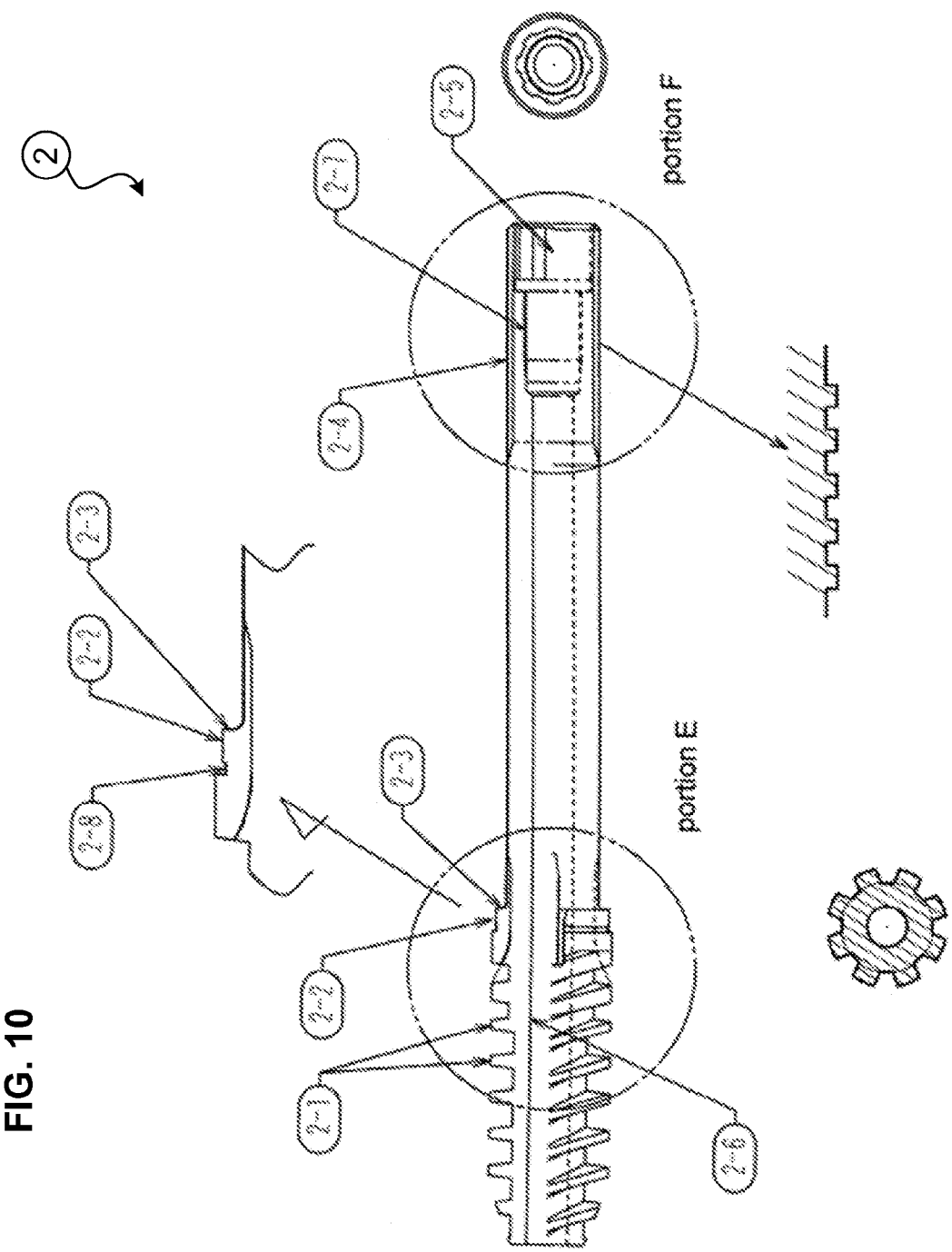
FIG. 10 is a cross-sectional view of an alternative embodiment of a lag screw.
Figure 11:
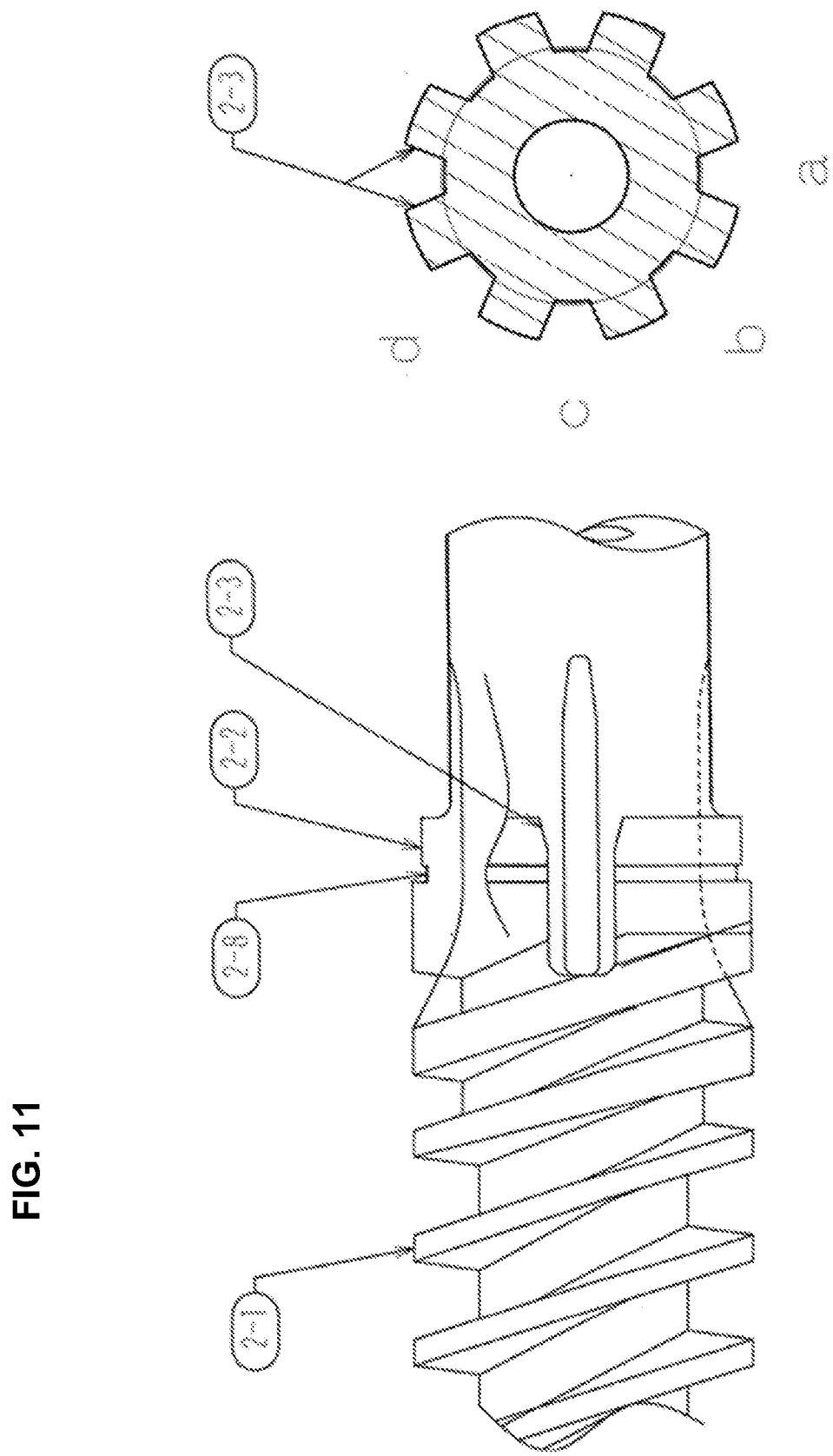
FIG. 11 is an enlarged detailed view 1 of portion E in FIG. 10, illustrating a male thread rear portion and the grip bar guide groove of a guide ring press-fitting portion of the lag screw.
Figure 12:
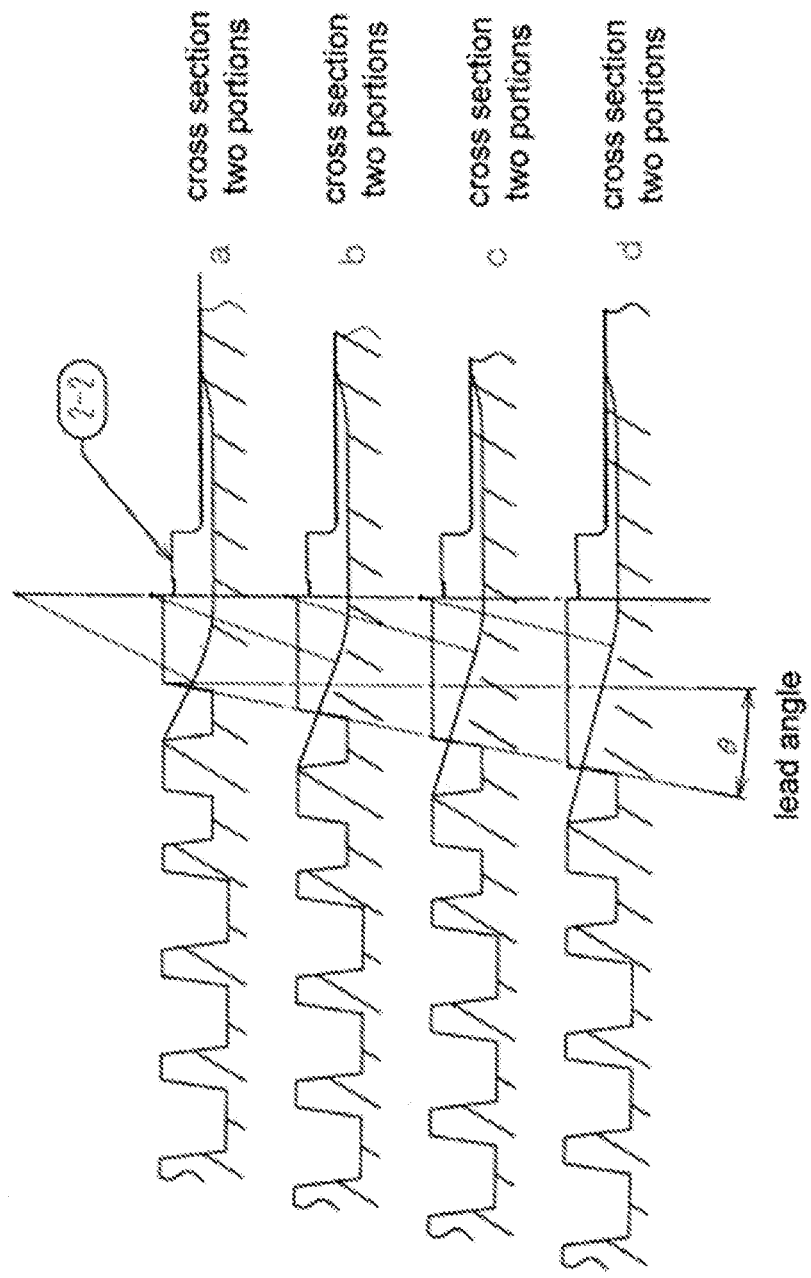
FIG. 12 is an enlarged detailed view 2 of portion E in FIG. 10, illustrating cross sections of the male thread rear portion of the lag screw and the grip bar guide grooves a, b, c, and d of the guide ring press-fitting part.
Figure 13:
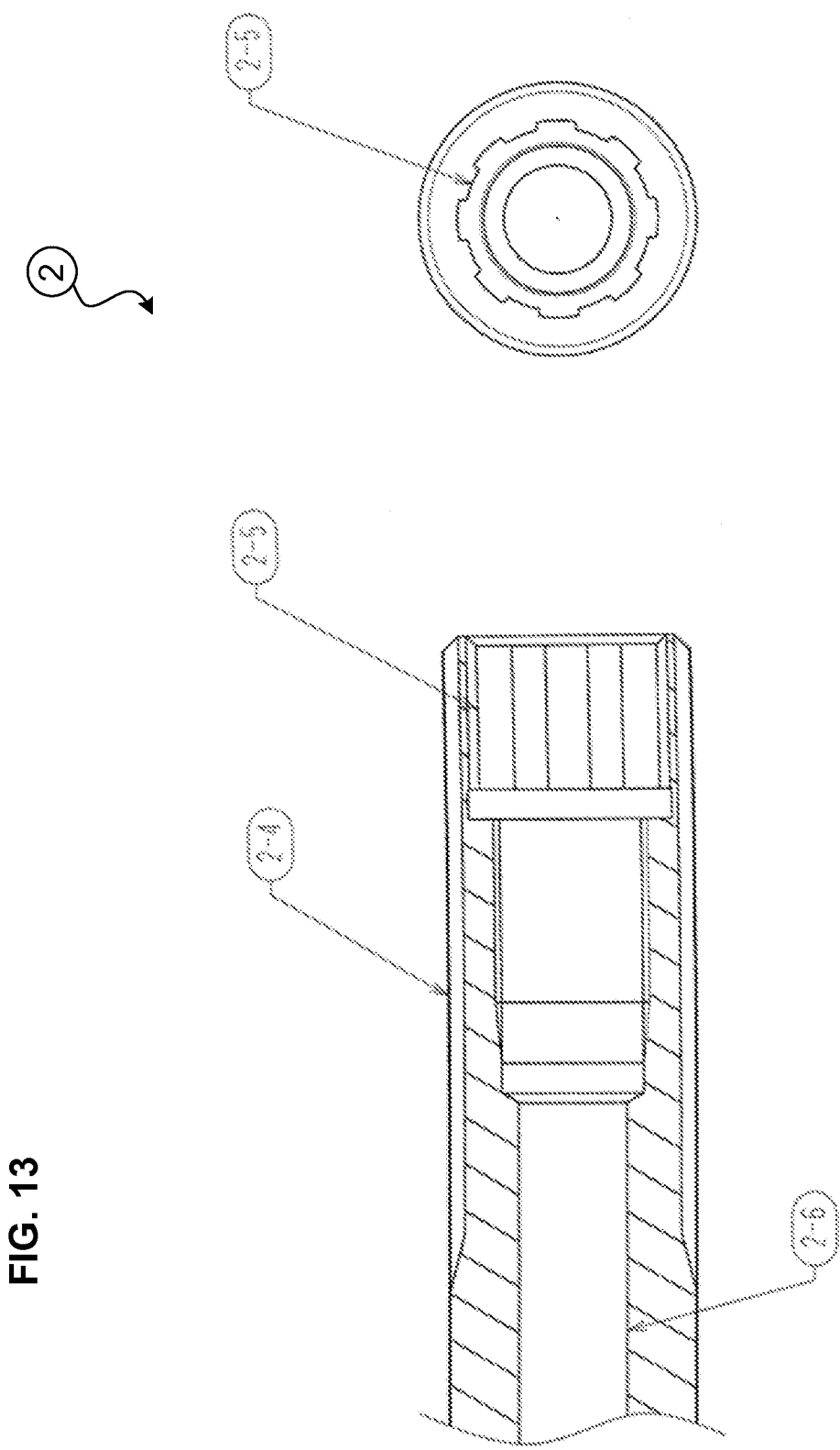
FIG. 13 is an enlarged detailed view of portion F of the lag screw in FIG. 10.
Figure 14:
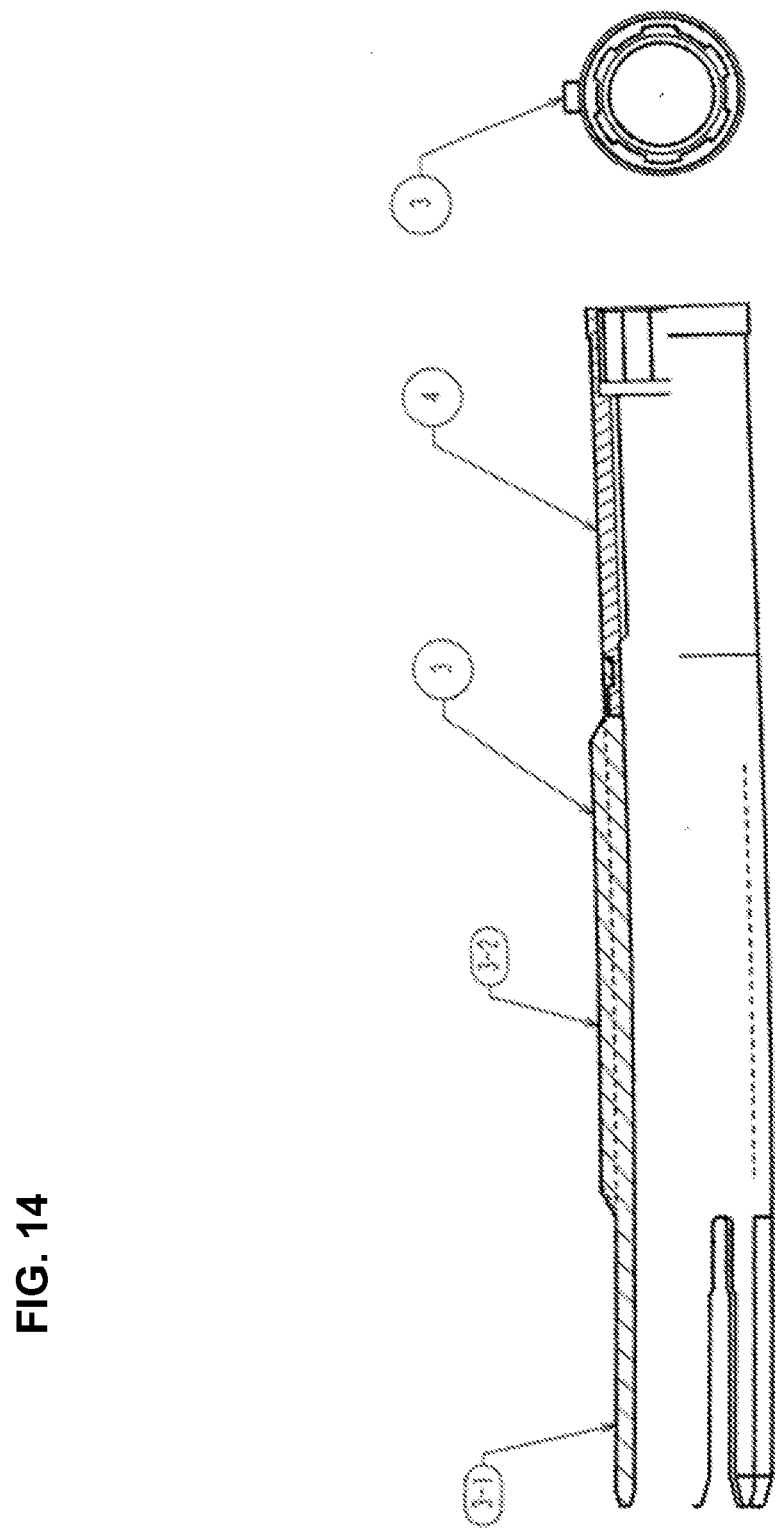
FIG. 14 is a cross-sectional view of an exemplary embodiment of a set of a key ring and a fastening nut.
Figure 15:
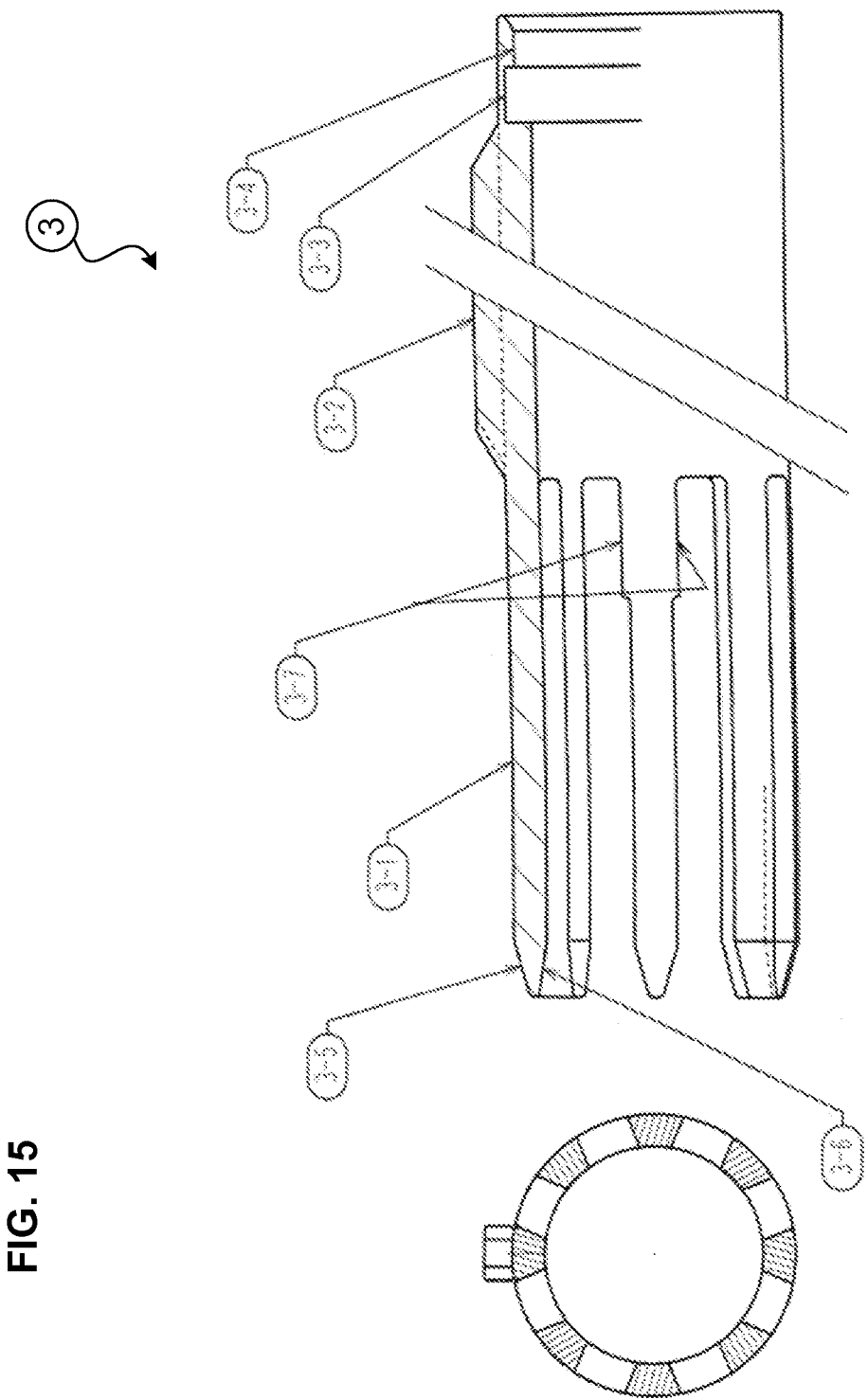
FIG. 15 is a cross-sectional view of an embodiment of a key ring.
Figure 16:
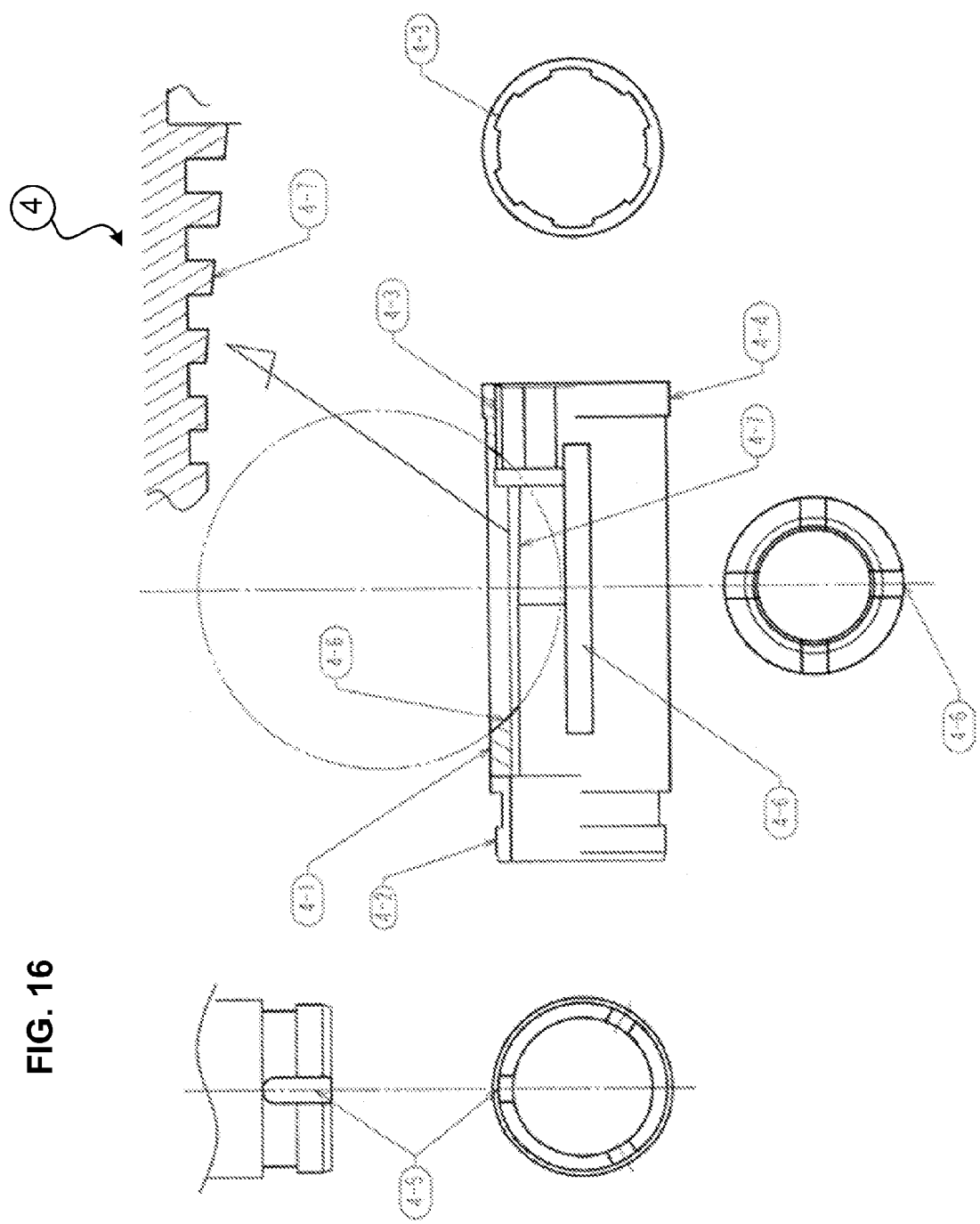
FIG. 16 is a cross-sectional view of an embodiment of a fastening nut.
Figure 17:
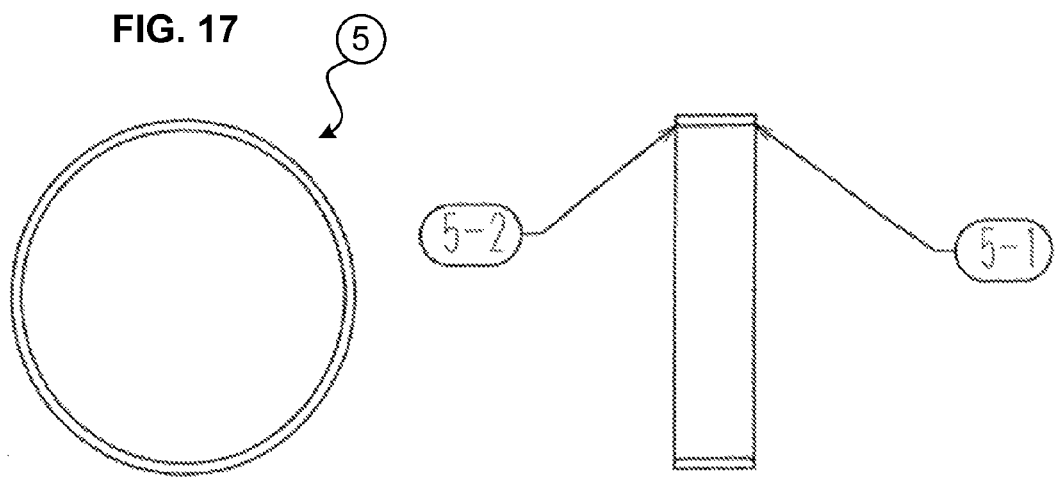
FIG. 17 is a general view of an embodiment of a guide ring.

The first embodiment of the present invention will now be described with reference to FIGS. 1, 2, 3, 4, 5, 6, 7, 8, 9, 10, 11, 12, 13, 14, 15, 16, and 17. FIG. 1 is a general cross-sectional view illustrating a state of insertion, in which a lag screw set is inserted into a nail 1. In this embodiment, the lag screw set may include a lag screw 2, a key ring 3, a fastening nut 4, and a guide ring 5. FIG. 2 represents a partial detailed view of portion A shown in FIG. 1. FIG. 3 is a general cross-sectional view illustrating a state in which the lag screw set is engaged with the nail 1 with key and is screwed into a predetermined position in a bone head part. FIG. 4 is a general cross-sectional view illustrating a final state at the advance end, in which the lag screw 2 and the key ring 3 are slidingly engaged with each other and grip bars 3-1 of the key ring 3 are opened and are biting into a cancellous bone due to the rotation of the fastening nut 4. FIG. 5 is a detailed view 1 of portion B in FIG. 4, illustrating the lag screw 2 and the grip bars 3-1 in the final state, wherein the grip bars 3-1 of the key ring 3 are fitted into and meshed with grip bar guide grooves 2-3 of a guide ring press-fitting portion 2-2 of the lag screw 2. FIG. 6 is a view taken along arrow C in FIG. 5, illustrating a state in which the grip bar 3-1 is fitted into and meshed with the grip bar guide groove 2-3. FIG. 7 is a detailed view 2 of the portion B in FIG. 4, illustrating the cross sections of the grip bar guide grooves a, b, c, and d corresponding to the grip bars 3-1 having a narrow bar shape, wherein the grip bars 3-1 of the key ring 3 are fitted into and meshed with the guide ling press-fitting portions 2-2, the grip bar guide grooves 2-3, and the male thread 2-1 in a circumferential spiral manner. FIG. 8 is a cross-sectional view of a rear portion of the lag screw set, illustrating a coupling state in which the lag screw 2 and the fastening nut 4, which are engaged with each other with screwing, are engaged with the key ring 3. FIG. 9 is a cross-sectional view generally illustrating a nail in accordance with a known art, wherein a key groove for slidingly coupling the key ring is provided in a lag screw attaching bore. FIG. 10 is a cross-sectional view generally illustrating the lag screw 2. FIG. 11 is a detailed view 1 of portion E of the lag screw 2 illustrated in FIG. 10, illustrating in detail a rear portion of a single to triple male thread 2-1 at a front end of the lag screw 2 and the guide ring press-fitting portion 2-2. FIG. 12 is a detailed view 2 of portion E of the lag screw 2 illustrated in FIG. 10, illustrating in detail a cross sections of the rear portion of the single to triple male thread 2-1 at the front end of the lag screw 2 and the guide ring press-fitting portion 2-2. FIG. 13 is a detailed view of portion F of the lag screw 2 illustrated in FIG. 10. FIG. 14 is a cross-sectional view generally illustrating a combination of the key ring 3 and the fastening nut 4, wherein the key ring 3 and the fastening nut 4 are fixedly engaged with each other in a rotatable manner. FIG. 15 is a cross-sectional view generally illustrating the key ring 3. FIG. 16 is a cross-sectional view generally illustrating the fastening nut 4. FIG. 17 is a diagram generally illustrating the guide ring 5.

In this embodiment, the lag screw 2 may include a single to triple male thread 2-1 at the front end thereof for biting into a bone head part. Due to a pressing force generated by twisting a pressing turning tool (not shown) inserted into a driving hole 2-5, such as a spline, provided at a rear end of the lag screw 2, the lag screw set including the lag screw 2, the key ring 3, the fastening nut 4, and the guide ring 5 is integrally advanced through a cylindrical hole with key of the nail 1 and is fixed.

As generally illustrated in FIG. 10 and partially illustrated in more detail in FIGS. 11, 12, and 13, the lag screw 2 may include the single to triple male thread 2-1, a guide ring press-fitting portion 2-2 with which a front end of grip bars 3-1 of the key ring 3 initially come into contact, and a grip bar guide grooves 2-3 with which side surface root engaging portions 3-7 provided on both sides of the grip bar of the key ring 3 engage. Further, the lag screw 2 includes the guide ring 5, a male thread 2-4 with which an engaging female thread 4-1 of the fastening nut 4 engages, the driving hole 2-5 such as a spline for a turning tool, and a guide hole 2-6.

A front end member of the lag screw 2 has a screw propulsion part consisting of the single to triple male thread 2-1. If the male thread is a double thread, the lag screw 2 proceeds for a distance that is twice as large as the pitch of the thread as it rotates for one revolution, enabling quick pressing of the thread. Also, the guide ring 5 is press-fitted into and attached by caulking to the guide ring press-fitting portion 2-2 provided in the rear of a thread end portion opposing a leading end of the single to triple male thread 2-1. When the grip bars 3-1 are initially inserted into the lag screw 2, a grip bar front end outer circumferential tapered portion 3-5 comes into contact with and is guided by an inner circumferential edge 5-1 of the guide ring 5 so as to proceed inwardly. When the key ring 3 further proceeds, the grip bars 3-1 sequentially come into contact with, in a spiral manner, bottom surfaces of the grip bar guide grooves 2-3 provided in the rear of the thread end portion of the single to triple male thread 2-1 in similar shapes, so that the grip bars 3-1 are maintained at a predetermined opening angle.

The guide ring 5 is press-fitted into the guide ring press-fitting portion 2-2 of the lag screw 2 and is then attached by caulking. When the grip bars 3-1 are inserted into the lag screw, the grip bar front end outer circumferential tapered portion 3-5 initially comes into contact with and is then guided by the inner circumferential edge 5-1 of the guide ring 5 so as to proceed inwardly. On the other hand, in a closingly returning process of the key ring 3 executed when the lag screw 2 and the key ring 3 need to be closingly returned after the grip bars 3-1 are fixed at set positions for making some adjustments to a surgery, for example, the outer circumference of the grip bars 3-1 that have opened comes into contact with and is guided by an internal circumferential edge 5-2 of the guide ring 5 so that the original outer shape of the grip bars 3-1 before being opened is recovered.

A rear end member of the lag screw 2 is integrally manufactured with the front end member, and the driving hole 2-5, such as a spline, into which a turning tool is inserted, is provided on an end surface of the lag screw 2.

The key ring 3 is a cylindrical member having a plurality of the grip bars 3-1 formed at a front end portion thereof by cutting off portions of a cylindrical front end at equal intervals. Each of the grip bars is in a shape of a narrow bar having a front end portion that is relatively narrow and a root portion that is a little larger than the front end portion, and is engaged with the grip bar guide groove 2-3 of the lag screw 2. In this embodiment, the number of the grip bars 3-1 is eight. The key ring 3 may also include a key 3-2 integrally formed therewith for engaging with the nail 1 to establish an anti-rotation mechanism, a fixing groove 3-3 for fixedly receiving a fixing convex portion 4-2 of the fastening nut 4 in a rotatable manner, the side surface root engaging portions 3-7 provided on both sides of the grip bar 3-1 for slidingly engaging with both side surfaces of the grip bar guide 2-3 provided on the guide ring press-fitting portion 2-2 of the lag screw 2, and the grip bar front end outer circumferential tapered portion 3-5 for assisting a smooth sliding contact for enabling easy insertion of the grip bar 3-1 in a radial outer circumferential direction.

Because the key 3-2 of the key ring 3 slidingly engages with a key groove 1-2 of the nail, the lag screw set integrally including the lag screw 2, the key ring 3, and the fastening nut 4 can slide with respect to the nail 1 while being prevented from rotating by the key 3-2. Also, as the key ring 3 proceeds in an axial direction, a plurality of the grip bars 3-1 formed at the front end of the key ring and having a narrow bar shape with the length of 5-25 mm initially come into contact with an inner circumference of the guide ring 5 by the grip bar front end outer circumferential tapered portion 3-5 so as to be pushed into the grip bar guide grooves 2-3. Thus, the grip bars 3-1 can be easily open at a predetermined appropriate angle and inserted into a cancellous bone to achieve a strong holding power.

The fastening nut 4 is also a cylindrical member and includes a female thread 4-1, which is a double female thread in this particular case, at an inner cylindrical center portion thereof for engaging with the male thread 2-4, which is a double male thread in this particular case, of the lag screw 2, the fixing convex portion 4-2 fixedly engaged with the fixing groove 3-3 in a rotatable manner, a driving hole 4-3, such as a female spline, into which a turning tool is inserted for advancing the key ring 3 in the lag screw set, and a retaining projection 4-4.

The technical scope of this invention is not limited to the above described embodiment, and various modifications can be made without departing from the gist of the invention.

Second Invention

Master Screw-Type Screw Apparatus

Figure 18:
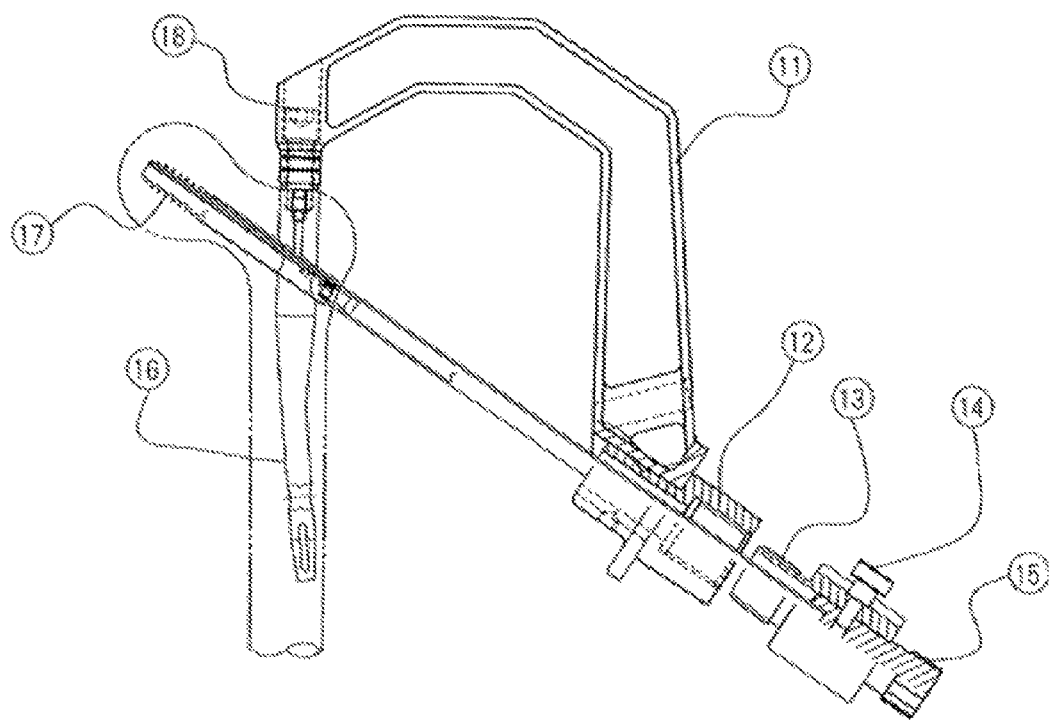
FIG. 18 is a general configuration diagram of an embodiment of a master screw driving-type screw apparatus in accordance with a second aspect of the present invention.
Figure 19:
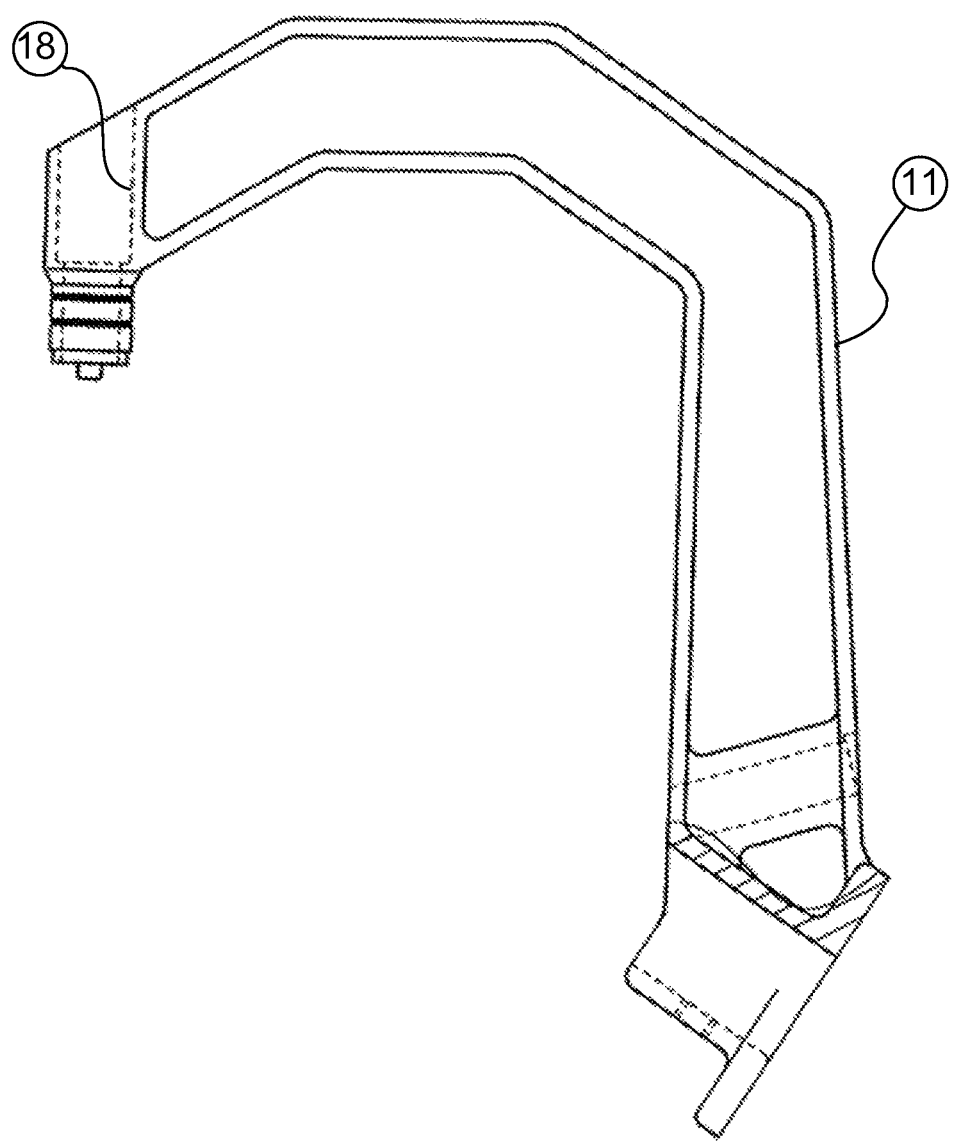
FIG. 19 is a general view of an embodiment of a guide apparatus body (frame) in accordance with a second aspect of the present invention.
Figure 20:
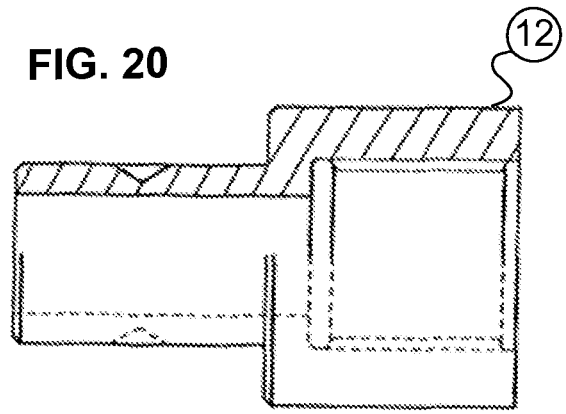
FIG. 20 is a general view of an embodiment of a stationary receiving boss in accordance with a second aspect of the present invention.
Figure 21:
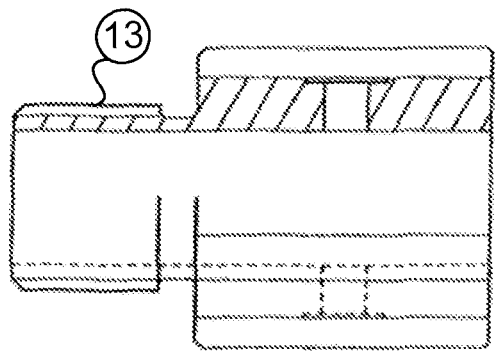
FIG. 21 is a general view of an embodiment of a master screw driving knob in accordance with a second aspect of the present invention.
Figure 22:
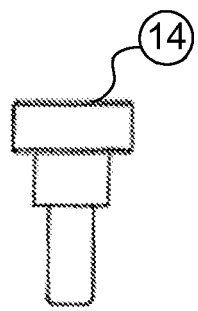
FIG. 22 is a general view of an embodiment of a connecting pin in accordance with a second aspect of the present invention.
Figure 23:
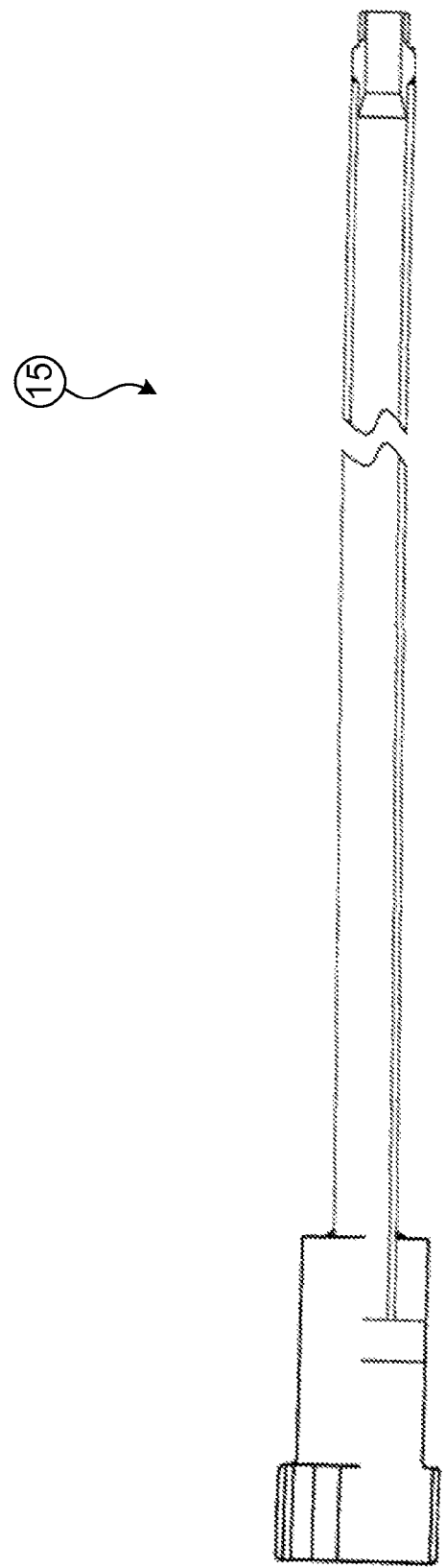
FIG. 23 is a general view of an embodiment of a lag screw driving sleeve in accordance with a second aspect of the present invention.
Figure 24:
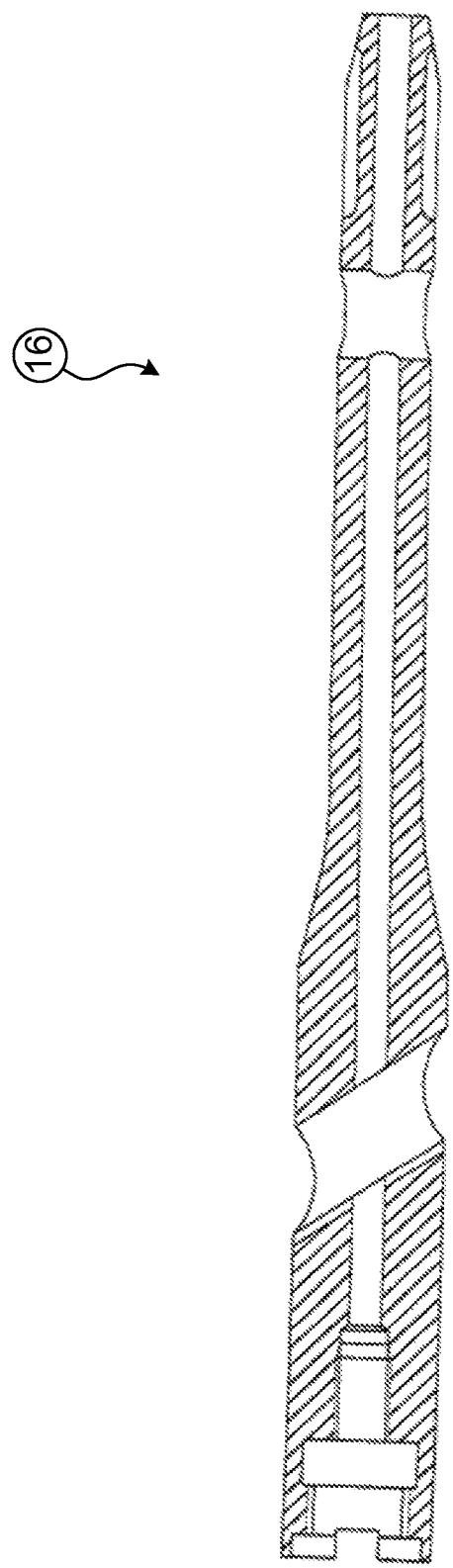
FIG. 24 is a general view of an embodiment of a nail in accordance with a second aspect of the present invention.

The second embodiment of the present invention will now be described with reference to FIGS. 18, 19, 20, 21, 22, 23, 24, and 25. FIG. 18 is a general configuration diagram of a master screw-type screw apparatus for a lag screw set 17 according to the first embodiment. As shown in this figure, in the screw apparatus of the current embodiment a frame 11 and a nail 16 in accordance with a conventional art are used. FIG. 19 is a general view of the frame 11. FIG. 20 is a general view of a stationary receiving boss 12 having a master screw female thread. FIG. 21 is a general view of a master screw driving knob 13 having a master screw male thread. FIG. 22 illustrates a general view of a connecting pin 14 that interrupts and establishes a connection between the master screw driving knob 13 and a lag screw driving sleeve 15. A general view of the lag screw driving sleeve 15 and a general view of a conventional art nail 16 are respectively shown in FIGS. 23 and 24. FIG. 25 is a general view of the lag screw set 17 which is used for improving the conventional art.

Figure 26:
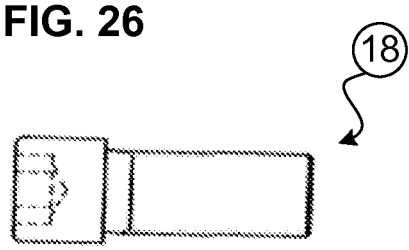
FIG. 26 is a general view of an embodiment of a coupling bolt in accordance with a second aspect of the present invention.

After fixing the stationary receiving boss 12 having the master screw female thread formed therein to the frame 11 of a conventional art by using a screwing method or the like, this set of the frame 11 and the stationary receiving boss 12 is fastened to the nail 16, which is inserted into a base portion of a femur in advance by using another method, with the coupling bolt 18 (shown in FIG. 26) so as to be oriented in a particular direction.

Next, with a guide wire hole for the lag screw set 17 created in a cancellous bone of the femur and a bone head portion, a set of the lag screw set 17 and the lag screw driving sleeve 15 coupled to each other with spline or the like is inserted into and set in the nail.

In the next step, while the aforementioned set including the lag screw driving sleeve 15 and the master screw driving knob 13 are connected to each other with the connecting pin 14, a front end of the master screw male thread of the master screw driving knob 13 is applied to and meshed with the master screw female thread of the stationary receiving boss 12. When the master screw driving knob 13 is rotated, the lag screw set 17 correspondingly advances according to the same lead as the master screw male thread. Thus, accurate and reliable tapping is executed.

When an osteosynthesis operation of a femur is completed, the connecting pin 14 can be removed so that the master screw driving knob 13 and the lag screw driving sleeve 15 can rotate freely. The lag screw driving sleeve 15 can then be pulled off without affecting the lag screw set 17.

Finally, a set of the frame 11 can be detached from a femur osteosynthesis operation apparatus by removing the coupling bolt 18.

The technical scope of this invention is not limited to the above described embodiment, and various modifications can be made without departing from the gist of the invention.

By using the lag screw according to the first aspect of the present invention, the lag screw can be assembled to the nail in a short period of time by screwing the lag screw only in one axial direction without using special expertise, and a bone fracture can be reliably fixed without loosening. Furthermore, a mechanism for retaining the lag screw is also provided. Also, by using the master screw-type screw apparatus according to the second aspect of the present invention for driving a lag screw, the lag screw can be accurately screwed in a short period of time with light force by screwing the lag screw only in one axial direction without requiring special expertise, and a bone fracture can be reliably fixed.

What is claimed is:

1. An osteosynthesis apparatus for proximal femur fracture comprising a nail for fixing a portion of a proximal femur fracture and a lag screw set with a key, the lag screw set being fittingly inserted into a cylindrical through hole drilled on a nail shaft of the nail at a predetermined inclined angle, the osteosynthesis apparatus comprising:
   a. the nail having a cylindrical shape and including the cylindrical hole drilled thereon at one inclined angle for receiving the lag screw set having a hollow cylindrical shape;
   b. a lag screw having a hollow cylindrical shape and including a single to triple male thread provided on a front outer circumferential portion thereof as a biting front end for osteosynthesis, a cylindrical projection provided in a rear of a thread end portion of the single to triple male thread, a groove provided on the cylindrical projection for engaging with a key ring, a male thread for engaging with a fastening nut, and a driving hole provided at a rear end portion for a turning tool;
   c. the key ring having a cylindrical shape and including a cylindrical inner circumferential portion for slidingly fitting on an outer circumference of the lag screw, a plurality of grip bars in a narrow bar shape having a length of 5 to 25 mm, the grip bars being provided on a front outer circumferential portion of the key ring so as to radially open during surgery, a groove portion formed on a rear inner circumferential portion of the key ring, and a key for slidingly engaging with a key groove of the nail;
   d. the fastening nut having a cylindrical shape and including a female thread formed at an inner circumference portion thereof for engaging with the male thread at a rear portion of the lag screw, a caulking portion provided on a front end outer circumference portion thereof for being bent inward, and a driving hole, for advancing a key ring set; and
   e. the lag screw set including the lag screw, the key ring, and the fastening nut, the lag screw being slidingly fitted into an inner circumferential hole of the key ring set from a front of the key ring set in a central axial direction thereof, the key ring set being configured by fixedly engaging the caulking portion at a front end inner circumferential portion of the fastening nut with the groove portion at the rear inner circumferential portion of the key ring so that the key ring and the fastening nut can rotate freely with respect to each other, the lag screw and the fastening nut being combined by engaging the male thread at a rear portion of the lag screw and the female thread of the fastening nut for approximately three windings of the threads, so that the lag screw set can be integrally advanced toward the nail by using a turning tool inserted into the driving hole provided at the rear end portion of the lag screw and then be stopped at a predetermined position with respect to a bone to be joined, and the key ring can then be advanced by rotating the fastening nut, causing the grip bars to radially open due to the fact that the grip bars come into contact with the grooves on the cylindrical projection of the lag screw and a thread surface of the lag screw while each of the grip bars of the key ring fits to and engages with both side surfaces of each of the grooves of the lag screw,
   wherein the lag screw and the fastening nut are completely fixed to each other due to an interference of engagement of approximately three windings at a trailing end of the male thread at the rear portion of the lag screw and approximately three windings at a trailing end of the female thread of the fastening nut and thus do not rotatingly loosen, while the lag screw set is movable smoothly with respect to the nail in an axial anteroposterior direction.

2. The osteosynthesis apparatus for proximal femur fracture according to claim 1, wherein the nail has a cylindrical shape and includes a nail body having a proximal end portion having the cylindrical hole drilled at one inclined angle with a key groove at a top portion thereof and a jig attaching hole, a distal end portion having a diameter smaller than that of the jig attaching hole of the proximal end portion and including a nail fixing hole, and a guide hole formed at a central axis portion of the nail body.

3. The osteosynthesis apparatus for proximal femur fracture according to claim 1, wherein the osteosynthesis apparatus is configured such that, by inserting a turning tool into the driving hole provided at the rear end portion of the lag screw in a hexagonal shape or the like and rotating the turning tool, the biting front end of the lag screw having a multiple thread is screwed to a predetermined position in a cancellous bone of a bone head part while the key ring set proceeds with the lag screw, and by succeedingly rotating the fastening nut, the plurality of grip bars in a narrow bar shape smoothly come in contact with the cylindrical projection provided in the rear of the thread end portion and then open at an angle.

4. The osteosynthesis apparatus for proximal femur fracture according to claim 1, wherein an open setting groove is provided on an outer circumferential surface of each of the grip bars for setting an angle of the opening of the grip bars in an outer radial direction, so that the grip bars formed at a front end portion of the key ring proceeding with respect to the lag screw initially come into contact with the cylindrical projection provided in the rear of the thread end portion of the thread at a front end of the lag screw, then sequentially come into contact with a thread surface, and open radially at an angle.

5. The osteosynthesis apparatus for proximal femur fracture according to claim 1, wherein both side surfaces of each of the grooves of the cylindrical projection of the lag screw fit and engage with each of the grip bars of the key ring to fix the rotation of the lag screw.

6. The osteosynthesis apparatus for proximal femur fracture according to claim 1, wherein the lag screw set including the lag screw, the key ring, and the fastening nut is coupled to the nail with key, so that the lag screw set does not rotate with respect to the nail but is able to move in the hole drilled on the nail anteroposteriorly in a central axial direction thereof.

7. The osteosynthesis apparatus for proximal femur fracture according to claim 1, wherein a projection is provided on a rear end outer circumferential portion of the fastening nut for preventing the lag screw set from coming out of the nail.

* * * * *